(12) United States Patent
Liu et al.

(10) Patent No.: US 7,233,034 B2
(45) Date of Patent: Jun. 19, 2007

(54) HYDROGEN PERMEABLE PROTECTIVE COATING FOR A CATALYTIC SURFACE

(75) Inventors: Ping Liu, Irvine, CA (US); C. Edwin Tracy, Golen, CO (US); J. Roland Pitts, Lakewood, CO (US); Se-Hee Lee, Lakewood, CO (US)

(73) Assignee: Midwest Research Institute, Kansas City, MO (US)

( * ) Notice: Subject to any disclaimer, the term of this patent is extended or adjusted under 35 U.S.C. 154(b) by 0 days.

(21) Appl. No.: 11/161,874

(22) Filed: Aug. 19, 2005

(65) Prior Publication Data

US 2007/0039372 A1    Feb. 22, 2007

(51) Int. Cl.
*H01L 27/14* (2006.01)

(52) U.S. Cl. .............. 257/252; 257/1; 338/34; 422/90; 436/144; 73/23.2; 73/23.4; 73/31.05

(58) Field of Classification Search ............... None
See application file for complete search history.

(56) References Cited

U.S. PATENT DOCUMENTS

| | | | |
|---|---|---|---|
| 5,030,742 A | 7/1991 | Tieke | |
| 5,338,708 A | 8/1994 | Felten | |
| 5,367,283 A | 11/1994 | Lauf et al. | |
| 5,520,753 A | 5/1996 | Hunter | |
| 5,652,433 A | 7/1997 | Ouwerkerk et al. | |
| 5,668,301 A | 9/1997 | Hunter | |
| 5,670,115 A | 9/1997 | Cheng et al. | |
| 5,886,614 A | 3/1999 | Cheng et al. | |
| 6,006,582 A * | 12/1999 | Bhandari et al. | 73/23.2 |
| 6,029,500 A | 2/2000 | Tom | |
| 6,073,478 A | 6/2000 | Kuriakose et al. | |
| 6,120,835 A | 9/2000 | Perdieu | |
| 6,160,278 A | 12/2000 | Liu et al. | |
| 6,185,344 B1 | 2/2001 | Bevenot et al. | |
| 6,265,222 B1 | 7/2001 | DiMeo, Jr. et al. | |
| 6,535,658 B1 * | 3/2003 | Mendoza et al. | 385/12 |
| 6,634,213 B1 * | 10/2003 | O'Connor et al. | 73/31.06 |

* cited by examiner

*Primary Examiner*—Sue A. Purvis
*Assistant Examiner*—Scott R. Wilson
(74) *Attorney, Agent, or Firm*—Paul J. White

(57) ABSTRACT

A protective coating for a surface comprising a layer permeable to hydrogen, said coating being deposited on a catalyst layer; wherein the catalytic activity of the catalyst layer is preserved.

24 Claims, 1 Drawing Sheet

HYDROGEN PERMEABLE PROTECTIVE COATING FOR A CATALYTIC SURFACE

CONTRACTUAL ORIGIN

The United States Government has rights in this invention under Contract No. DE-AC36-99GO10337 between the U.S. Department of Energy and the National Renewable Energy Laboratory, a Division of Midwest Research Institute.

TECHNICAL FIELD

A hydrogen permeable protective coating for a surface, preferably a catalytic metal-based surface, wherein the dissociation of hydrogen into atomic hydrogen is preserved, namely, the catalytic activity is allowed to proceed without contamination. One such embodiment includes a protective coating for a catalytic metal-based surface (e.g., a sensor or other detecting device) for sensing the presence of a hydrogen gas. More particularly, a protective coating for a catalytic metal-based hydrogen sensor having a hydrogen, catalyst palladium (Pd) layer, (however, the layer may also comprise or be composed of platinum group metals and their alloys, e.g., palladium copper alloys and palladium silver alloys.) Another embodiment includes applications to the catalytic activity of platinum group metal surfaces involving hydrogen dissociation for fuel cell anodes.

BACKGROUND

Hydrogen gas is a clean, non-polluting fuel and chemical reagent, which is currently used in many industries. With the demand for hydrogen growing every year and the fact that hydrogen is explosive at only a four (4%) percent concentration in air, the ability to detect hydrogen gas leaks economically and with inherent safety is desirable and could facilitate commercial acceptance of hydrogen fuel in various applications. For example, hydrogen-fueled passenger vehicles will require hydrogen leak detectors to signal the activation of safety devices such as shutoff valves, ventilating fans, and alarms. In fact, such detectors will be required in several key locations within a vehicle—namely, wherever a leak could pose a safety hazard. Therefore, it is critically important to carefully measure, monitor, and strictly control hydrogen wherever and whenever it is used.

The real and perceived hazards of hydrogen fuel use, its production, and storage require extensive safety precautions. Local, state and federal codes must be put in place before any serious movement can be made towards a hydrogen based energy future. Currently, commercial hydrogen detectors are not practical for widespread use, particularly in transportation industry applications, because commercial detectors are too bulky, expensive, and dangerous.

There exist several hydrogen sensors having a palladium layer that is particularly attractive for transportation industry applications. These hydrogen sensors are termed Hydrogen Field Effect Transistors (HFET), thick film (e.g., incorporating a palladium alloy paste), thin film, and fiber optic. The HFET construction uses a thin film of Pd as the metal contact controlling the device. The presence of hydrogen results in the migration of atomic hydrogen to the interface between the metal film and the insulator, which results in a change in the output of the device that is scaled to hydrogen concentration. The thick film device uses a thick film Pd alloy paste to form a four-resistor network (i.e., a Wheatstone bridge) on a ceramic substrate. The configuration is such that two opposed resistors result in a change in resistivity of the thick film material and a shift in the balance point of the bridge, which can be scaled to the hydrogen concentration. The thin film device is equivalent in design to the thick film, with only much thinner films (typically vacuum deposited) used as the resistors.

The fiber optic hydrogen sensor is a gasochromic-type (i.e., one that changes color when activated by hydrogen) sensor and is available in a variety of configurations with coatings, typically either palladium or platinum, at the end of an optical fiber that sense the presence of hydrogen in air. When the coating reacts with the hydrogen, the optical properties of the coating are changed. Light from a central electro-optic control unit is projected down the optical fiber where the light is either reflected from the sensor coating back to a central optical detector, or is transmitted to another fiber leading to the central optical detector. A change in the reflected or transmitted intensity indicates the presence of hydrogen. While the fiber optic detector offers inherent safety by removing the application of electrical power and by reducing signal-processing problems by minimizing electromagnetic interference, critical detector performance requirements (i.e., for all four configurations described above) include high selectivity, response speed, and durability as well as potential for low-cost fabrication. The optical senor is not necessarily limited to a fiber optic delivery system but may be included on any optical element.

Unfortunately, all of the conventional catalytic metal-based hydrogen sensors have the potential for degradation in their performance over time due to mechanisms that are inherent in their construction, a result of their cyclic interaction with hydrogen, or contamination from impurities in the environments in which they will be used. While various attempts have been made to protect the palladium or platinum catalytic surfaces, these attempts have not significantly improved sensor performance. Therefore, a need exists to limit degradation thereby allowing hydrogen sensors to operate over extended periods of time in the presence of contaminants.

Another application is in the proton electrolyte membrane (PEM) fuel cell. This fuel cell is an electrochemical device that produces electricity from a combined chemical reaction and electrical charge transport. The device uses a simple chemical process to combine hydrogen and oxygen into water, producing an electric current in the process. At the anode, hydrogen molecules are dissociated by a metallic catalyst (usually platinum) into hydrogen atoms, which eventually gives up electrons to form hydrogen ions. The electrons travel through an external circuit to produce usable electric energy while the hydrogen ions are transported internally to the cathode where they both combine with oxygen to form water. The platinum catalyst of the fuel cell anode is subject to degradation by contaminants similar to that of catalytic metal-based hydrogen sensors. Application of a protective coating to the surface of the anode of the platinum catalyst to prevent fouling and maintain the catalytic activity of hydrogen dissociation is advantageous to fuel cell performance.

The foregoing examples of the related art and limitations related therewith are intended to be illustrative and not exclusive. Other limitations of the related art will become apparent to those of skill in the art upon a reading of the specification and a study of the drawing.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

An exemplary, preferably amorphous (i.e., a lack of long-range crystalline order) hydrogen permeable protective coating for catalytic metal surfaces is disclosed. This exemplary embodiment has unique and novel application for sensing the presence of hydrogen gas in an environment. The exemplary coating material comprises a layer permeable to hydrogen with the layer being deposited on a surface, for example, a sensor between the metal catalyst layer and the environment.

Accordingly, an exemplary protective coating for a surface comprises a layer permeable to hydrogen, the coating being deposited on a catalyst layer, wherein the catalytic activity of the catalyst layer is preserved. In the disclosed exemplary protective coating for the catalyst layer is a carbon material which is preferably amorphous; it may be deposited using a vapor deposition process, preferably a plasma enhanced chemical vapor deposition process and the protective coating is preferably deposited at room temperature. The catalyst layer is composed of platinum group metals, and/or platinum group metals and their alloys. The exemplary protective coating further includes a chromogenic layer underlying the catalyst layer; and a substrate layer underlying the chromogenic layer. However, it will be apparent to those skilled in the art that the protective layer may be understood to overlie the catalyst layer. Under these circumstances the catalyst layer would accordingly overlie the chromogenic layer; and the chromogenic layer would overlie a substrate layer.

Additionally, a sensor for sensing the presence of hydrogen gas in an environment is disclosed, comprising: a protective layer permeable to hydrogen; a catalyst layer deposited on said protective layer; a chromogenic layer deposited on said catalyst layer; and a substrate layer deposited on said chromogenic layer; wherein the catalytic activity of the catalyst layer is preserved.

Further, an exemplary method for protecting a catalytic metal-based sensor for sensing the presence of hydrogen in an environment is disclosed by depositing a protective layer on the sensor, wherein the protective layer is permeable to hydrogen.

In addition to the exemplary aspects and embodiments described above, further aspects and embodiments will become apparent by reference to the drawings and by study of the following descriptions.

BRIEF DESCRIPTION OF THE DRAWING

An exemplary embodiment is illustrated in the referenced figure of the drawing. It is intended that the embodiment and figure disclosed herein is to be considered illustrative rather than limiting.

DETAILED DESCRIPTION

Figure 1:
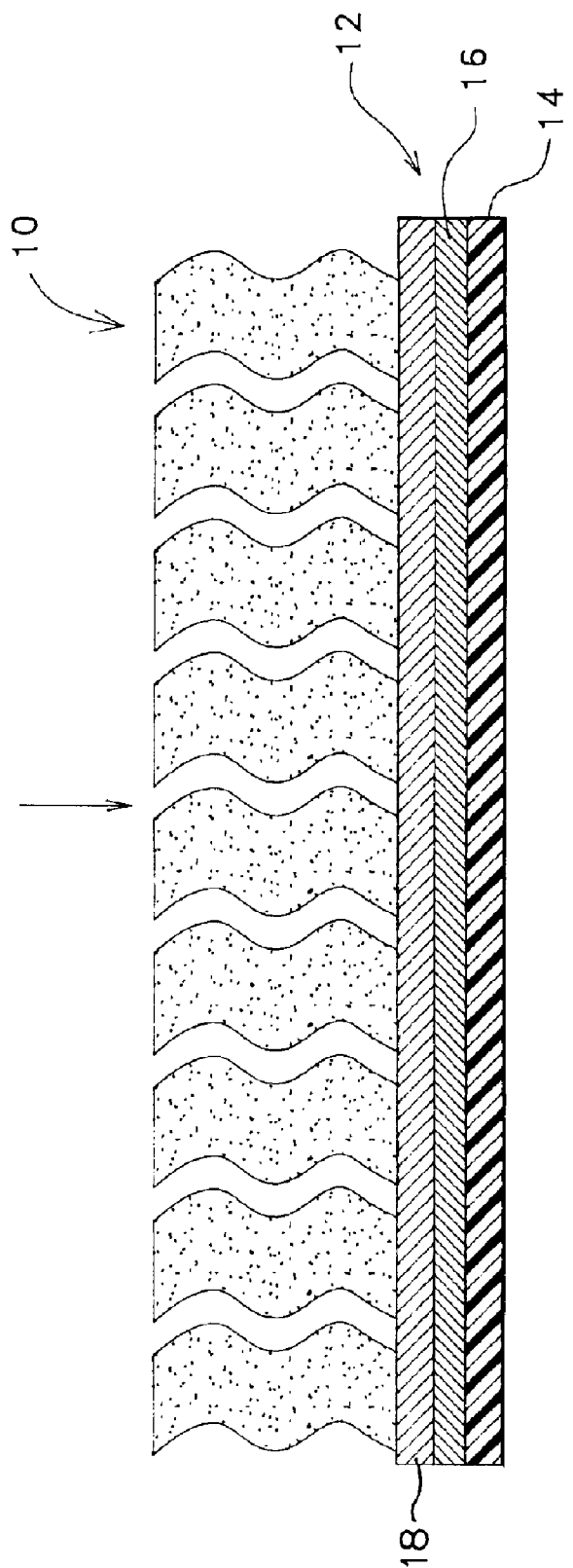
FIG. 1 is a sectional view of an exemplary protective coating for a catalytic metal-based hydrogen sensor.

As illustrated in FIG. 1, an exemplary protective coating (material or layer), indicated generally as 10, for catalytic metal (including gasochromic) sensor 12 is used in sensing the presence of hydrogen gas (as indicated by the arrow). While sensor 12 can detect different types of gas on a surface or in an environment, including, but not limited to, rooms, buildings, chemical process plants, refineries, etc., the construction and design of sensor 12 especially suits the sensing of hydrogen leaks in hydrogen-fueled vehicles or similar applications. Therefore, in discussing exemplary protective coating 10 of sensor 12, applicants will particularly describe sensor 12 in conjunction with transportation (namely, vehicle) use. It should be noted, however, that any variety of catalytic metal-based sensors including, but not limited to, HFET, thick film, thin film, and fiber optic sensors, are envisioned and contemplated by those skilled in the art.

The sensor 12 has a substrate layer 14, a chromogenic layer 16, and a catalyst layer 18. The catalyst layer 18 underlies protective coating layer 10; chromogenic layer 16 underlies catalyst layer 18; and substrate layer 14 underlies chromogenic layer 16. The catalyst layer 18 is preferably composed or comprised of palladium, platinum, or their alloys, such that when exposed to the atmosphere it is reactable to the presence of hydrogen in the environment. While catalyst layer 18 has been described as being comprised of palladium, platinum, or their alloys, catalyst layer 18 may be composed of other appropriate materials for example, the platinum group metals (platinum, palladium, rhodium iridium, ruthenium, and osmium). Moreover, many of their alloys are exceptionally good catalysts as will be apparent to those skilled in the art. Among these, palladium and its alloys work exceptionally well for applications in hydrogen sensors, because of their ability to dissociate molecular hydrogen and their very high diffusion constants for atomic hydrogen, allowing rapid transport through or to the sensing element and/or material.

During the sensing operations of sensor 12 in an environment, the reaction between the hydrogen gas and chromogenic layer 16 or the catalyst layer 18 changes the chromogenic layer or the catalyst layer (or both) material's optical properties allowing sensor 12 to sense the presence of hydrogen. Protection of the chromogenic layer 16 and catalyst layer 18 from any contaminants present in the environment (while simultaneously allowing hydrogen permeation) is important for the detection of hydrogen gas in the environment. If the chromogenic layer 16 or the catalyst layer 18 is compromised (e.g., the catalytic hydrogen dissociation sites on the surface of the catalyst becomes poisoned) by contaminants, sensor 12 will fail to function properly leading to the possible failure of hydrogen gas detection in the environment.

Therefore, protective coating 10 is both a protective (i.e., shielding) and hydrogen permeable layer deposited on the catalyst layer 18 to protect the chromogenic layer 16 and the catalyst layer 18 of sensor 12. Preferably, the protective coating 10 is a hydrogen permeable carbon coating deposited on the catalyst layer 18 by using any number of vapor deposition processes, however, the preferred method is a plasma-enhanced chemical vapor deposition process, preferably at room temperature. As an example of the plasma-enhanced chemical vapor deposition process, the radio frequency (RF) is 150 W, the substrate 14 temperature is thirty (30°) degrees C., the system pressure is 0.6 torr. Ethylene is the processing gas and the flow rate is twenty (20) sccm. Once deposited, the protective carbon coating 10 possess the characteristics of an amorphous structure, which is permeable to hydrogen but filters the environment's air prior to any contaminants reaching the chromogenic layer 16 and catalyst layer 18. Those skilled in the art will appreciate that a wide variety of system parameters (power, pressure, temperature, etc.) will result in variety of successful coatings.

As will be understood by a person skilled in the art, the protective coating 10 can be deposited or applied to catalyst layer 18 by a variety of techniques at a variety of temperatures. Describing the protective coating 10 as being deposited on the catalytic layer 18 by a chemical vapor deposition technique at room temperature is only one of many different deposition techniques and other techniques will be apparent to those skilled in the art.

The carbon coating 10 is permeable to hydrogen but can act effectively as a diffusion barrier to contaminant gas molecules, such as hydrocarbon, carbon monoxide, and sulfur-bearing gases, including others. Application of the protective carbon coating 10 to the palladium or platinum catalytic layer 18 of sensor 12 greatly improves the stability and durability of the sensor with a minimum compromise or degradation in sensor performance. It should be noted that the carbon coating 10 is also applicable to protect gas separation devices having platinum group metals or their alloys as the catalytic and/or functional layer.

The protective coating 10 extends or increases the lifetime of sensor 12 in the presence of harmful contaminants and provides effective protection of palladium—and platinum-based hydrogen sensors. In fact, the protective coating 10 is also applicable wherever a platinum group metal or alloy layer is used and its use is not limited to gasochromic hydrogen sensors.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

What is claimed is:

1. A protective coating for a surface comprising a layer permeable to hydrogen, said coating being deposited on a catalyst layer; wherein the catalytic activity of the catalyst layer is preserved;
wherein the layer permeable to hydrogen comprises a carbon material that is amorphous.

2. The protective coating of claim 1, wherein the layer permeable to hydrogen is deposited using a vapor deposition process.

3. The protective coating of claim 2, wherein the vapor deposition process is a plasma enhanced chemical vapor deposition process.

4. The protective coating of claim 1, wherein the layer permeable to hydrogen is deposited at room temperature.

5. The protective coating of claim 1, wherein the catalyst layer is composed of platinum group metals.

6. The protective coating of claim 1 wherein the catalyst layer is composed of platinum group metals, or their alloys.

7. The protective coating of claim 1, further comprising a chromogenic layer underlying said catalyst layer.

8. The protective coating of claim 7, further comprising a substrate layer underlying said chromogenic layer.

9. A sensor for sensing the presence of hydrogen gas in an environment, the sensor comprising:
a protective layer permeable to hydrogen, wherein the protective layer comprises a amorphous carbon layer;
a catalyst layer deposited on said protective layer;
a chromogenic layer deposited on said catalyst layer; and
a substrate layer deposited on said chromogenic layer;
wherein the catalytic activity of the catalyst layer is preserved.

10. The sensor of claim 9, wherein the protective layer is deposited using a vapor deposition process.

11. The sensor of claim 10, wherein the vapor deposition process is a plasma enhanced chemical vapor deposition process.

12. The sensor of claim 9, wherein the protective layer is deposited at room temperature.

13. The sensor of claim 9, wherein the catalyst layer is constructed of platinum group metals.

14. The sensor of claim 9, wherein the catalyst layer is constructed of platinum group metals, or their alloys.

15. A protective coating for a surface, comprising a layer of amorphous carbon permeable to hydrogen, said amorphous carbon layer being deposited on a catalyst layer by a vapor deposition process, said catalyst overlying a chromogenic layer, said chromogenic layer overlying a substrate layer, wherein the catalytic activity of the catalyst is preserved.

16. The protective coating of claim 15, wherein the catalyst layer is an anode for a fuel cell.

17. The protective coating of claim 15, wherein the vapor deposition process comprises a plasma-enhanced chemical vapor deposition process.

18. The protective coating of claim 17, wherein the vapor deposition process uses ethylene as a processing gas.

19. A sensor for sensing the presence of gas in an environment, comprising:
a protective layer permeable to the gas, wherein the protective layer comprises amorphous carbon; and
a catalyst layer underlying the protective layer, wherein the catalytic activity of the catalyst layer is preserved.

20. The sensor of claim 19, further comprising a chromogenic layer underlying the catalyst layer.

21. The sensor of claim 19, wherein the protective layer acts as a diffusion barrier to at least hydrocarbon, carbon monoxide, and sulfur-bearing gases.

22. The sensor of claim 19, wherein the protective layer is deposited directly upon the catalyst layer using vapor deposition.

23. The sensor of claim 22, wherein the vapor deposition is carried out at a temperature of about 30° C.

24. The sensor of claim 19, wherein the catalyst layer comprises a material selected from the group consisting of palladium, platinum, rhodium iridium, ruthenium, osmium, and alloys of these materials.

* * * * *